United States Patent [19]  
Schofield

[11] 4,104,585  
[45] Aug. 1, 1978

[54] MEASUREMENT OF IMPURITY CONCENTRATION IN LIQUIDS
[75] Inventor: John Wardman Schofield, Hitchin, England
[73] Assignee: National Research Development Corporation, London, England
[21] Appl. No.: 762,923
[22] Filed: Jan. 26, 1977

Related U.S. Application Data

[63] Continuation-in-part of Ser. No. 590,822, Jun. 26, 1975, abandoned.

[30] Foreign Application Priority Data

Dec. 23, 1974 [GB] United Kingdom .............. 55455/74

[51] Int. Cl.² ........................................ G01R 27/04
[52] U.S. Cl. ............................................. 324/58.5 C
[58] Field of Search ............ 324/58.5 C, 58 C, 58.5 B

[56] References Cited

U.S. PATENT DOCUMENTS

| | | | |
|---|---|---|---|
| 2,457,673 | 12/1948 | Hershberger | 324/58.5 C |
| 2,580,968 | 1/1952 | Sproull | 324/58 C |
| 2,597,327 | 5/1952 | Hollingsworth | 324/58 C |
| 2,792,548 | 5/1957 | Hershberger | 324/58.5 C |
| 2,964,703 | 12/1960 | Sargent et al. | 324/58 C X |
| 2,965,841 | 12/1960 | Smoll | 324/58.5 C |
| 2,972,104 | 2/1961 | Ward | 324/58.5 C X |
| 3,577,071 | 5/1971 | Collins | 324/58.5 B |
| 3,688,188 | 8/1972 | Bak et al. | 324/58.5 C |
| 3,737,770 | 6/1973 | Masson et al. | 324/58.5 C |

Primary Examiner—Stanley T. Krawczewicz  
Attorney, Agent, or Firm—Cushman, Darby & Cushman

[57] ABSTRACT

Apparatus for the measurement of the concentration of impurities in liquids comprising two microwave cavity resonators, means for enabling a standard sample of liquid to be coupled to one of the resonators to affect the resonant frequency thereof, means for enabling a sample of liquid under test to be coupled to the other resonator to affect the resonant frequency thereof, and means for mixing the outputs from the resonators to derive a difference frequency dependent on the difference in concentration of particles in the two samples.

5 Claims, 1 Drawing Figure

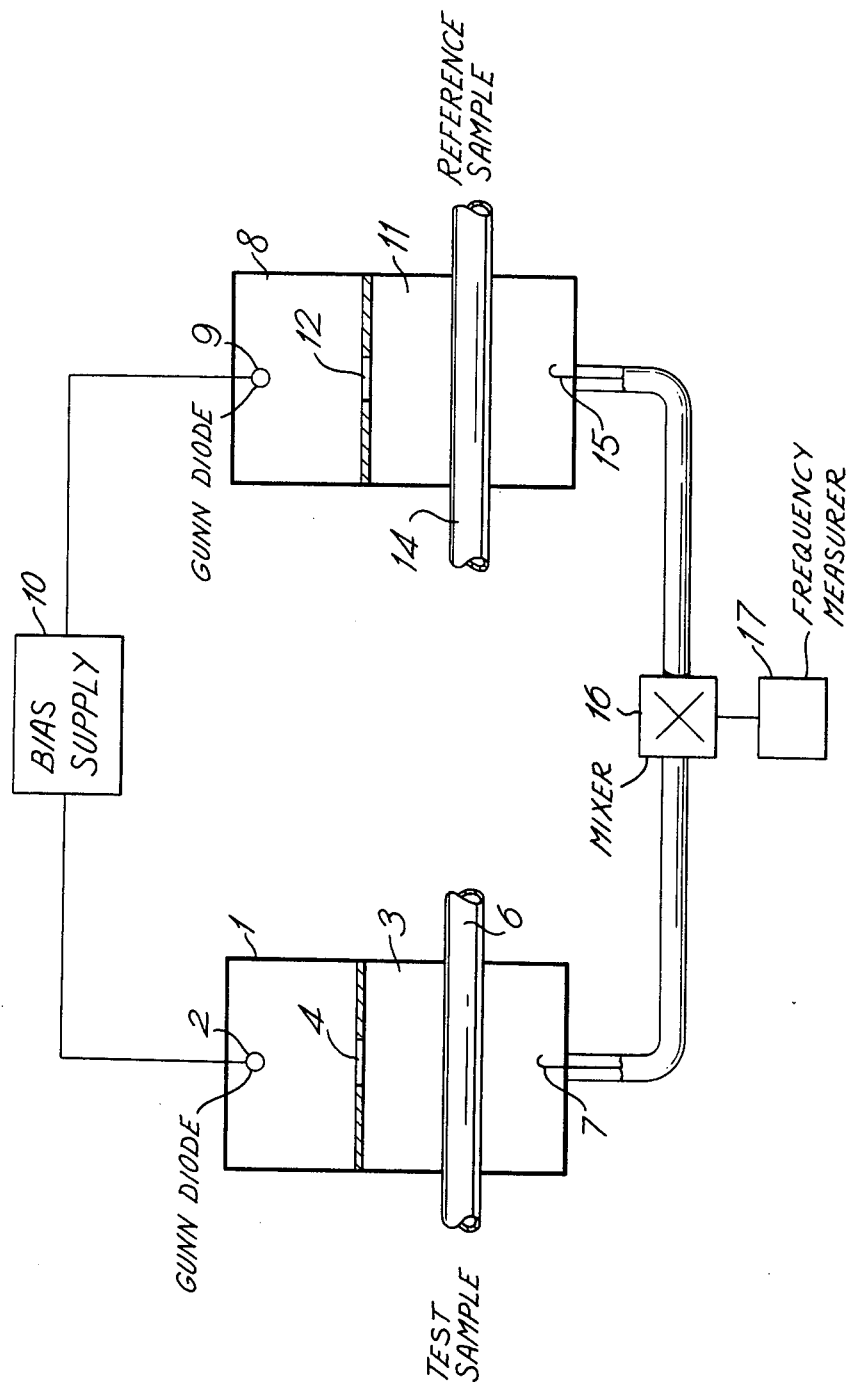

MEASUREMENT OF IMPURITY CONCENTRATION IN LIQUIDS

This invention relates to the measurement of the concentration of impurities in liquids and is a continuation-in-part of my co-pending application Ser. No. 590,822 filed June 26, 1975, now abandoned.

Conventional apparatus for the measurement of the concentration of impurities in the form of suspended particles uses optical methods the results of which are affected by the size of the particles that may be suspended and by the growth of films on the optical surfaces of the apparatus.

According to the invention apparatus for the measurement of the concentration of impurities in liquids comprises two microwave cavity resonators, two microwave generators each coupled to a respective cavity resonator, means for enabling a standard sample of liquid to be coupled to one of the resonators to affect the resonant frequency thereof, means for enabling a sample of liquid under test to be coupled to the other resonator to affect the resonant frequency thereof, and means for mixing the outputs from the resonators to derive a difference frequency dependent on the difference in concentration of impurities in the two samples.

Preferably the resonators are of similar dimensions and resonate at the same frequency. The resonators may conveniently be energised by Gunn diodes which are supplied from a common voltage source.

In carrying out the invention each reasonator may be coupled to a secondary cavity associated therewith and the samples are contained in the secondary cavities. The coupling between a resonator and its secondary cavity may be by means of an iris.

In order that the invention may be more fully understood reference will now be made to the drawing accompanying this specification the single FIGURE of which illustrates an embodiment thereof in diagrammatic form.

Referring to the FIGURE there is shown therein a first cavity resonator 1 energised by a Gunn diode 2 mounted therein. Adjacent to cavity 1 there is a secondary cavity 3 which receives microwave energy from cavity 1 through an iris 4. Cavity 3 is arranged to have mounted therein a tube 6 of a sample of water in which it is desired to measure the concentration of impurities. Tube 6 may be a simple test tube or else may be included in a flow-through system. A probe 7 is mounted in cavity 3 to extract microwave signals therefrom.

The resonant frequency of a cavity of fixed dimensions depends inter alia on the dielectric constant of the material in space within the cavity. The dielectric constant of water is about 80 for frequencies below its absorption edge while the dielectric constant of sludge solids is typically less than 5. Thus the dielectric constant of a water sample containing particles will be somewhere between these figures and will depend on the concentration of particles in the water sample. In the case of water contaminated by impurities such as oil similar results are obtained. Thus the extent to which the resonant frequency of cavity 3 is affected by the presence of a water sample therein depends on the concentration of impurities in that sample.

In order to provide a suitable reference frequency against which the frequency changes caused by impurities in a sample can be measured a further resonant cavity 8 is provided which contains a Gunn diode 9 resonant at the same frequency as diode 2 and both diodes 2 and 9 are supplied from a common voltage source 10 of say 10 volts. A secondary cavity 11 is coupled to resonator 8 through an iris 12. In like manner to cavity 3, cavity 11 is arranged to have mounted therein a tube 14 of water, preferably pure water, as a reference. Microwave energy in cavity 11 is extracted therefrom by means of a probe 15. The signals from probes 7 and 15 are mixed together in a mixer 16 and the frequency of the output therefrom is measured in a suitable device 17.

Resonator 1 and secondary cavity 3 for the sample under test are arranged to be of similar dimensions respectively to reference resonator 8 and its secondary cavity 11. Also to ensure that there are no dimensional differences arising out of difference in temperature between the cavities it is desirable to make both resonators and their secondary cavities out of a single block of aluminium for example.

If a sample of pure water is placed in tube 14 and the sample in tube 6 is unpolluted it will be seen that there will be no difference in the frequencies of the signals fed to mixer 16 and hence mixer 16 will provide a zero frequency output. However the presence of impurities in the water in tube 6 will alter the resonant frequency of the energy in cavity 3 to produce a frequency difference between the two inputs to mixer 16. Accordingly the frequency of the output from mixer 16 is a measure of the concentration of impurities in tube 6. Frequency measuring device 17 can comprise a counter or a ratemeter.

The degree of coupling between counter 1 and cavity 3 is determined by the size of the aperture in the iris 4 and this determines the magnitude of the frequency charge for a given concentration of impurities. Accordingly the size of the iris determines the sensitivity of the apparatus.

While the invention has been described with reference to the measurement of impurities in water, such impurities being for example suspended particles or oil in water the invention is equally applicable to the measurement of impurities in other liquids, for example water in oil.

I claim:

1. Apparatus for the measurement of the concentration of impurities in liquids comprising two microwave cavity resonators, two microwave generators each coupled to a respective cavity resonator, means for enabling a standard sample of liquid to be coupled to one of the resonators to affect the resonant frequency thereof, means for enabling a sample of liquid under test to be coupled to the other resonator to affect the resonant frequency thereof, and means for mixing the outputs from the resonators to derive a difference frequency dependent on the difference in concentration of impurities in the two samples.

2. The apparatus as claimed in claim 1 in which the said two resonators are of similar dimensions and resonate at the same frequency.

3. The apparatus as claimed in claim 1 in which the two generators each comprise Gunn diodes which are supplied from a common voltage source.

4. The apparatus as claimed in claim 1 in which respective secondary cavities are associated with each resonator and the samples are contained in the secondary cavities.

5. The apparatus as claimed in claim 4 in which an iris coupling is provided between each resonator and its secondary cavity.

* * * * *